United States Patent [19]

Haywood

[11] Patent Number: 5,724,140

[45] Date of Patent: Mar. 3, 1998

[54] METHOD AND APPARATUS FOR DETERMINING THE QUALITY OF FLAT GLASS SHEET

[75] Inventor: James William Haywood, Ann Arbor, Mich.

[73] Assignee: Ford Motor Company, Dearborn, Mich.

[21] Appl. No.: 738,557

[22] Filed: Oct. 28, 1996

[51] Int. Cl.⁶ .................................................. G01B 11/30
[52] U.S. Cl. ........................ 356/371; 356/239; 356/445; 250/571
[58] Field of Search .................................. 356/238, 239, 356/371, 445; 250/571

[56] References Cited

U.S. PATENT DOCUMENTS 5,016,099  5/1991  Bongardt et al. .
5,126,579  6/1992  Breitmeier ............................. 356/382
5,210,592  5/1993  Bretschneider .
5,251,010  10/1993  Maltby, Jr. ............................. 356/371
5,471,307  11/1995  Koliopoulos et al. .................. 356/371

Primary Examiner—Frank G. Font
Assistant Examiner—Reginald A. Ratliff
Attorney, Agent, or Firm—Damian Porcari

[57] ABSTRACT

A method of determining the quality of flat glass sheet comprising the steps of illuminating a glass sheet with a light ray at an acute angle. A mask having alternating opaque and transparent portions is positioned to receive light from the ray after it has struck the glass sheet. The ray is moved to a first position on the sheet to a second position and causes the light ray to move along the mask. The light passing through the mask is collected and the duration of the collected light is measured. The duration of light passing through the mask is correlated to the quality of the glass sheet that has been inspected.

15 Claims, 3 Drawing Sheets

METHOD AND APPARATUS FOR DETERMINING THE QUALITY OF FLAT GLASS SHEET

BACKGROUND OF THE INVENTION

The present invention relates to a method of determining the optical quality of flat glass sheets. More specifically, the invention relates to a method of determining the quality of flat glass sheets by measuring the velocity of a light beam as it travels along a segmented mask.

SUMMARY OF THE RELATED ART

It is desirable to determine the optical quality of flat glass sheets made by the float process. Determining flaws or imperfections on the surface or within the glass before it is manufactured into finished articles saves both the cost and energy of manufacturing the article. It also allows the glass manufacturing process to be quickly corrected. It is desirable to determine both the surface quality of the flat glass sheet as well as irregularities or imperfections within the glass. These imperfections or irregularities cause optical distortion. It is therefore a further desire to determine the location on the glass where the irregularities or imperfections are occurring to assist in correcting the manufacturing process. Determining the location on the glass with the flaws allows the acceptable portion of the glass to be used for finished products while only the unacceptable portion is scrapped.

One method of determining the optical quality of flat glass is taught in U.S. Pat. No. 5,016,099 (Bongaret) issued May 14, 1991. The Bongaret patent teaches illuminating a moving piece of flat glass with a wide beam light source. Light strikes the glass at acute angles of between 57° and 85°. Light passes through the glass and becomes projected on a screen positioned underneath the glass. Distortions in the glass cause diverging and converging exit rays. Areas of the glass having converging exit rays project a brighter image on the projection screen. Areas of the glass having diverging exit rays project a darker image. A video camera views the projection screen through the glass and creates a signal that corresponds to the light and dark areas on the projection screen. The signal is processed in an analog to digital converter and processor and compared to stored values in the computer memory. Deviations from stored values are displayed as defects on a computer screen or printer. The system relies on the light intensity measurement to determine the optical quality of the glass. The intensity measurement in the Bongardt patent is complicated because a light beam is spread across the entire width of the glass sheet. Some float glass lines run glass having a width of 4 meters. It is difficult an evenly illuminate an area this wide. Further, the intensity measurement is taken through the glass sheet and is degraded by ambient light and distortions caused from passing the reflected image through the glass a second time. When the glass is tinted, these intensity measurements become even more difficult. Further complications in measuring the reflected intensity are caused by a layer of hot air above the glass. This thermal layer affects the image seen by the camera and obscures the reflected intensity.

Yet another complicating factor of the Bongardt patent is that the image plane, that is the distance between the glass and the projection screen, must be less than the focal length of the distortion. If the image plane exceeds the focal length of the distortion, then the converging areas will pass through the focal point and appear as diverging areas. Because the system primarily concentrates on the brighter areas (the areas having greater convergence), the overall resolution of the system is lower. Areas of glass that have very high distortion will also have a very short distortion focal length. These areas will not cause the bright bands on the focal screen.

It is also possible to determine the surface quality of flat glass using a reflective beam as taught in U.S. Pat. No. 5,210,592, (Bretschneider), issued May 14, 1991. The Bretschneider patent teaches reflecting two parallel rays off the surface of a glass plate and measuring the impact point of the rays. The Bretschneider patent teaches moving two parallel rays across the surface of the glass sheet. The entire laser, reflector and collector assembly is transversely scanned across a glass plate surface. Manually moving this assembly across the surface of the glass plate significantly slows data collection on glass surface quality.

It is desirable to provide a method and apparatus that determines both surface irregularities and internal imperfections within a glass sheet. It is a further desire of the present invention to provide a apparatus and method for measuring glass optical quality in ambient light and provide a display of the physical location of imperfections or irregularities. It is also desirable to place the measuring apparatus away from the glass a distance greater than the focal length of the largest optical distortion. These and other objects, features and advantages of the present invention will become more apparent to those skilled in the art upon reference to the attached drawings and following description.

SUMMARY OF THE INVENTION

The present invention relates to a method of determining the quality of flat glass sheets comprising the steps of illuminating a glass sheet with a light ray at an acute angle. A mask having alternating opaque and transparent portions is positioned to receive light from the ray after it has struck the glass sheet. The ray is moved from a first position on the sheet to a second position and causes the light ray to move along the mask. The light passing through the mask is collected and the duration of the collected light is measured. The duration of light passing through the mask is correlated to the quality of the glass sheet that has been inspected. The device is useful for both measuring the surface quality and imperfections or defects contained within the glass sheet.

A rotating mirror causes a light beam to traverse the glass sheet at a nearly constant acute angle. A light collector collects light exiting the mask and transmits it to a light detector. The light detector measures the interval and duration of each light pulse and determines the optical quality of the glass by comparing these measured durations and intervals to known values.

Invention may also measure optical distortions of glass having a focal length less than the distance between the glass surface and the mask. Using an alternative embodiment of the invention, a mask having a semi-transparent portion between the transparent and opaque portions may be used to resolve areas of high optical distortions where the focal length of the distortion is less than the distance between the glass sheet and the mask.

The invention uses the speed at which the light ray travels along the mask to determine the optical quality of the glass sheet. Distortions within the glass or irregularities on the glass surface cause the light ray striking the mask to bend and strike the mask at a location different than had there been no optical distortion. The differences in the speed of the beam as it travels along the mask is related to the optical quality of the glass.

DETAILED DESCRIPTION OF THE PREFERRED EMBODIMENTS

Figure 1:
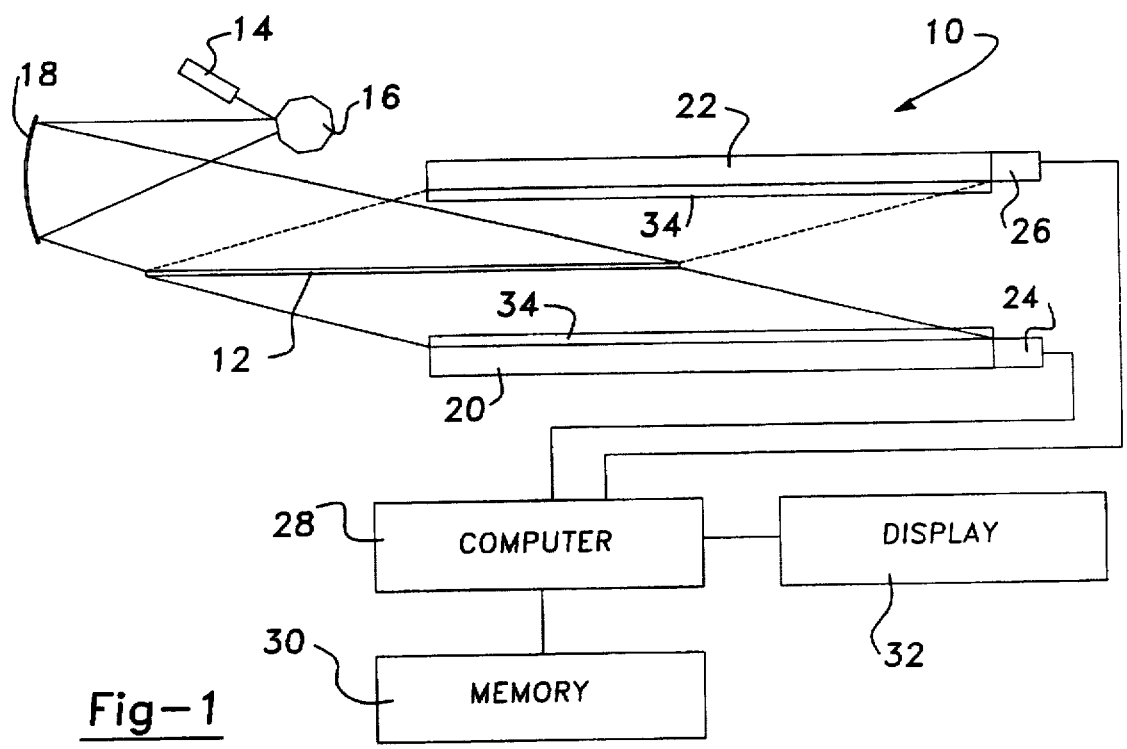
FIG. 1 is schematic representation of the method and apparatus of the present invention measuring both the surface quality of the glass and optical defects within the glass.
Figure 2:
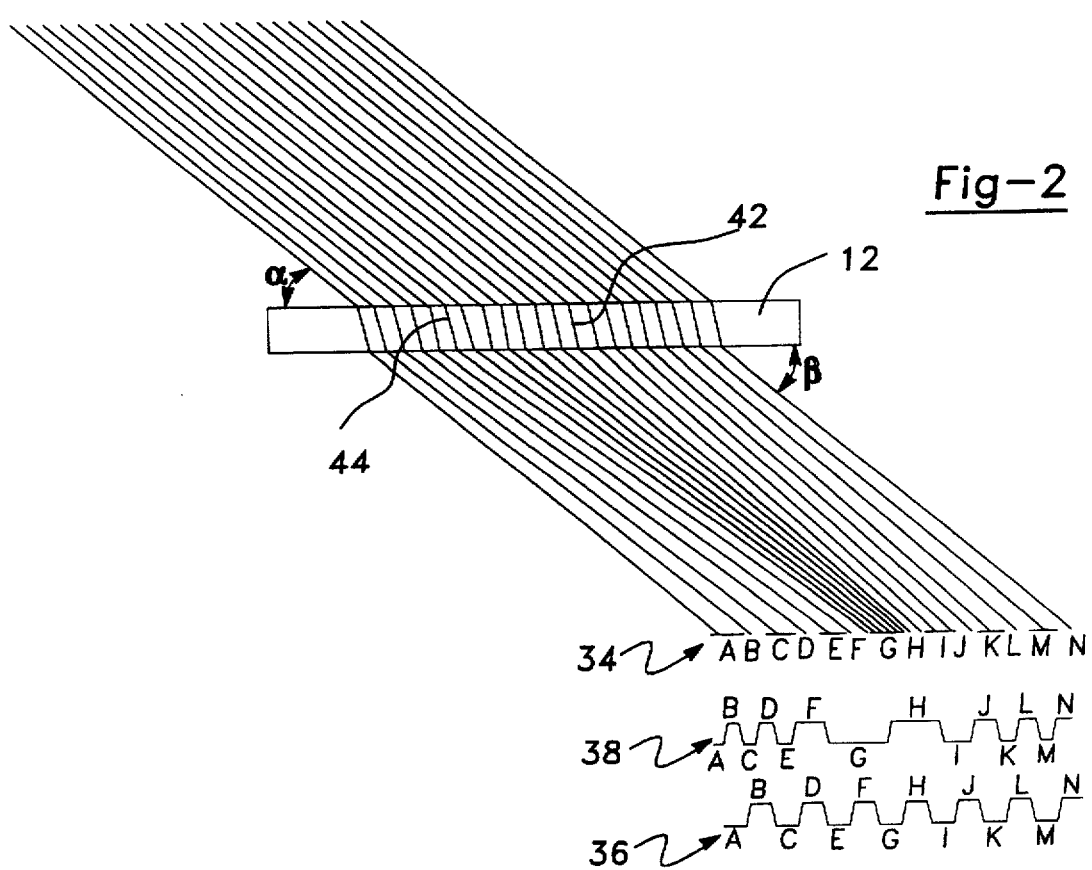
FIG. 2 is a detailed schematic representation of light rays striking a binary mask.

The present invention teaches a method of determining the optical quality of a glass sheet by scanning a light ray across the glass sheet at a constant acute angle. An apparatus 10 measures the optical quality of a glass sheet before it is cut as illustrated in FIGS. 1–2. A glass sheet 12 is manufactured by a float process and forms a flat planner sheet upwards of 4 meters in width. The sheet travels along a moving conveyer at 0.4–1.7 feet per second. When the glass sheet is sufficiently rigid so as to be transported across an open area, its optical quality may be inspected by a light ray passing through the glass sheet. It is generally desirable to place as much of the assembly 10 above the glass sheet in the event that the glass breaks or fractures. A collimated light beam, for example a laser beam 14, having a power output of 15 mwatts and an optical wavelength of 632.1 nm admits a ray of coherent light on a rotating mirror 16. The number of sides and the rotational speed of the mirror 16 is dependent upon the width of the glass sheet 12 and the desired resolution of the optical measurement. More sides or a faster spin rate increase the resolution of the apparatus 10. Light reflected by the mirror 16 strikes a parabolic mirror 18. The parabolic mirror 18 is shaped so as to cause light rays to strike the glass sheet 12 at a nearly constant angle across the width of the glass sheet. Light rays passing through the glass sheet 12 are collected by an internally reflecting light transmission pipe 20. Light reflected from the surface of the glass sheet 12 are collected by a light transmitting pipe 22. It is possible to simultaneously measure both surfaces of the glass sheet 12 by either using two lasers or one single laser and two parabolic mirrors. Light collected in the light pipes 20, 22 are transmitted to photodetectors 24, 26.

The output of the detectors 24, 26 are fed into a general purpose computer 28. The computer 28 measures the output values of the detectors 24, 26 and compares them with values stored in a memory 30. Variations from these stored values are sent to display means 32 and indicate the optical quality of the glass sheet 12.

The amount of distortion is determined by the amount the light ray is bent as it either passes through the glass sheet or is reflected by the glass sheet surface. A glass having no distortion or surface irregularities reflects the light or passes the light at a constant angle. A mask 34 having alternating transparent portions and opaque portions is placed jaxaposed to the light collectors 24, 26. The alternating opaque and transparent portions interrupt the light rays as they passes through the mask and cause them to form a pulsed pattern. Glass having no optical distortion would form a uniform pulsed pattern. Optical distortion or surface irregularities are manifested by changes in the duration or interval of the pulses.

Figure 3:
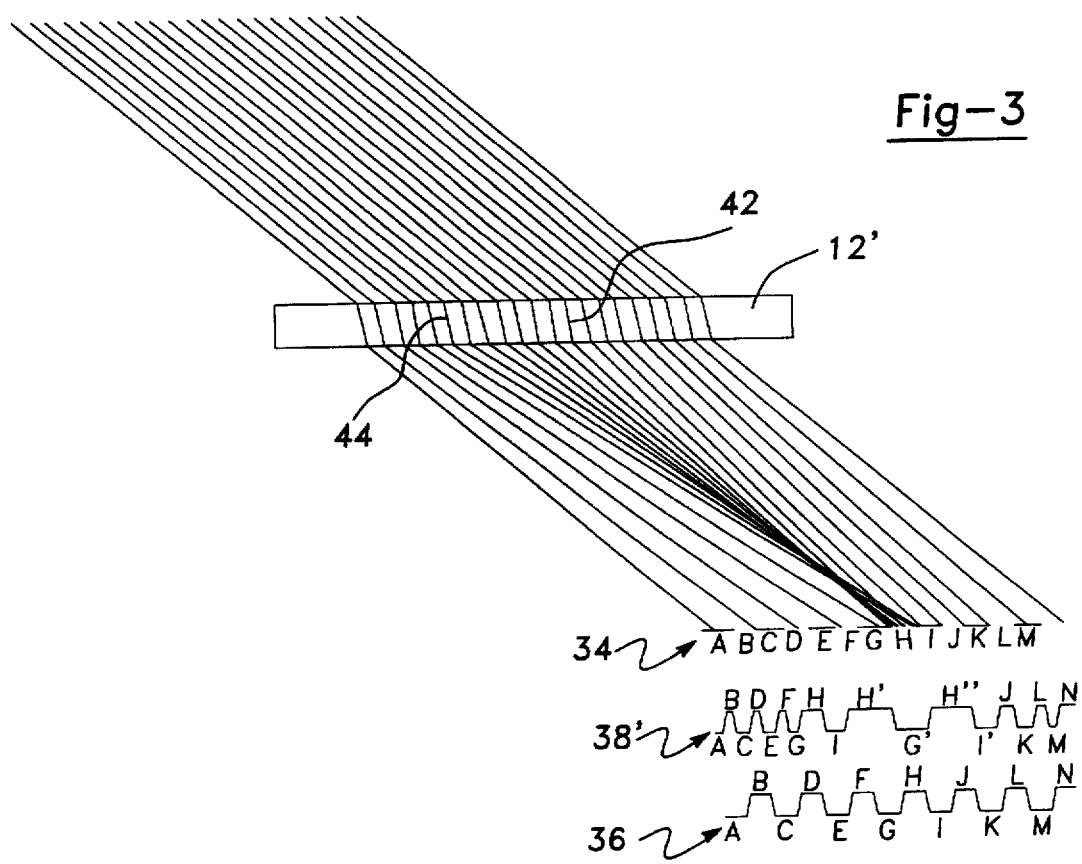
FIG. 3 is a detailed schematic representation of glass having a high optical distortion.

An example of these optical distortions is illustrated in FIGS. 2–3. These figures illustrate the optical distortion or irregularities within the glass. Similar measurements occur when measuring the surface irregularities of the glass. Light rays from the mirror 18 strike the glass at an acute angle between 45° and 85° degrees. The light rays pass through the glass sheet 12. Imperfections or irregularities internal to the glass sheet 12 cause the light rays to bend more or less than they would a piece of glass without flaws. This bending causes a convergence or a divergence in the light ray as it passes through the glass sheet 12. The amount of convergence or divergence may be measured as a function of time. The light ray is a collimated beam which is scanned along the surface of the glass sheet and traces a line from one edge of the glass sheet 12 to the other. If the glass sheet 12 had no optical distortions, then the entrance angle $\alpha$ would equal the exit angle $\beta$. Irregularities or distortions within the glass cause the exit angle to differ from the entrance angle. These differences may be measured as the speed at which the point light source travels along the mask 34.

Mask 34 comprises a series of alternating transparent and opaque portions. Opaque portions A, C, E, G, I, K and M do not allow the passage of light through the mask 34. Transparent portions B, D, F, H, J, L and N allow the passage of light. In the absence of optical distortion within the glass 12, the light passing through the transparent portions of the mask 34 would form a series of regular square-wave pulses as represented by the graph of signals 36. Signals 36 represent the signals of the photodetectors 24, 26 as they receive light from the collectors 20, 22. The output of the photodetectors is generally a zero voltage in the absence of light and a positive voltage in the presence of light. Regions A, C, E, G, I, K and M of signal 36 represent areas of no light and correspond in time as the light beam trace progresses from area A to area N on the mask 34. The signal 36 may either be measured when no glass is present or calculated analytically. A graph of signal 38 represents the output of detector 24 as the light rays pass through a sheet of glass 12 having optical distortion. Light rays striking portion A of the mask 34 cause a zero voltage reading represented as region A in signal 38. As the light moves along the glass sheet 12, the exit rays strike area B of the mask 34. Light passing through the area B of the mask 34 causes a positive voltage in the detector 24 and is displayed as a voltage pulse region B on the signal 38. The duration of the pulse at region B in signal 38 is shorter than the anticipated pulse at region B in signal 36. This is due to a distortion in the glass 12 which causes a divergence in the exit ray and increases the velocity of the exit ray as it traverses from portion A to portion N on the mask 34. The exit rays change from diverging to coverging as they strike the portion G on the mask 34. The period of time that the exit rays are incident on portion G of the mask 34 increases. This converging corresponds to a longer duration of zero voltage and is represented by region G in the signal 38.

The area of the glass sheet 12 marked 40 includes imperfections which cause diverging distortion. The area of the glass marked 42 causes converging distortion. The computer 28 shown in FIG. 1, compares the measured signal 38 with the reference signal 36 and displays the optical quality of the glass. Both the physical location on the glass sheet and the type of distortion may be determined from this measurement. A timer measures the beginning and end of each scan based on the position of the rotating mirror or by sensing the location of the exit ray on the mask. The location of the ray may be sensed at a point beyond the edge of the glass by an area of the mask that has two or more adjacent transparent portions.

The invention as illustrated in FIGS. 1 and 2 is useful for measuring distortion in glass that has a focal length greater than the distance between the mask and the glass surface. It is possible that the focal length of the distortion is less than the distance between the mask and the glass surface thus causing the light rays exiting the glass to go back upon themselves as illustrated in FIG. 3. The glass sheet 12' has an area of high distortion at location 44. Rays exiting the glass sheet have a focal length less than the distance between the glass sheet and the mask 34. The exit rays that strike the mask 34 do not uniformity alternate between the transparent and opaque portions. In the example illustrated in FIG. 3, rays exiting the glass sheet 12' at location 44 are strongly converging and instead of continuing to region J after entering region I, instead go back into regions H and G. The rays do not pass totally through region G before changing direction and again going into region H and then on to regions I and J. Since the rays do not pass completely through the regions I and G, the distortion calculated for the regions after I may be incorrect since the pulse length will not be compared to the correct anticipated length; for example, region H' will be compared to region J, region G' to region K, and so on. To address these areas of high optical distortion or placing the mask 34 remote from the glass sheet 12', an alternative embodiment of the invention is proposed.

Figure 4:
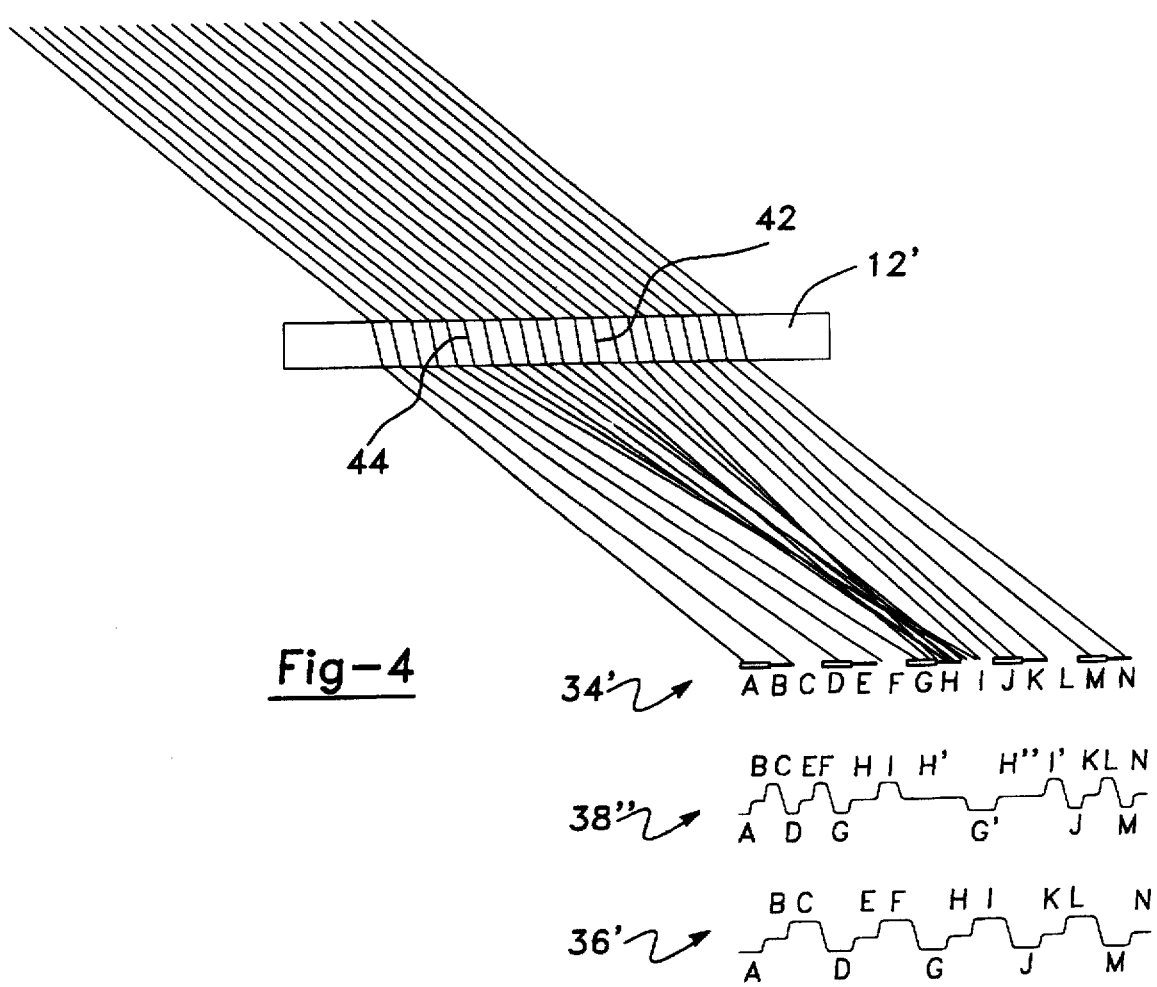
FIG. 4 is detailed schematic representation of an alternative embodiment of the present invention using a tertiary mask.

In FIG. 4, the mask 38' comprises a series of alternating transparent, semi-transparent and opaque portions. Opaque portions A, D, G, J, and M block the passage of light through the mask 38'. Semi-transparent portions B, E, H, and K and N allow a portion of the light exiting the glass sheet 12' to pass through the mask 38' at a reduced intensity. Transparent portions C, F, I and L allow the exit rays to pass through the mask 38' at full intensity. Using the same glass sheet 12' and the optical distortion thereof, the exit rays can be seen to pass from one area to another in the distortion signal 38". An anticipated signal with no distortion 36" alternates between no intensity at region A, intermediate intensity at region B and full intensity at region C. This pattern is repeated as the light travels along the mask 34'. But the distortion within the glass sheet 12' can be detected by measuring both the intensity and the duration of the light that passes through the mask 34'. After exiting region H, the ray enters region I but does not pass through it to region J and instead returns to region H. This change in direction is detected by the intensity of light changing from full transmission to a partial transmission instead of from full transmission to no transmission. When this change in the pattern of light intensity is detected, the apparatus is able to determine that the beam has reversed direction and to correctly compare region H' to the anticipated value for region H. The ray moving in the reverse direction enters region G after leaving region H, but does not go into region F. This again is shown by the pattern of light intensity changing back to the "normal" no transmission to partial transmission to full transmission to no transmission pattern. The apparatus again is able to detect the change in the direction of the beam's motion and correctly compare regions H', I' and so on to the correct anticipated values.

Using a measurement of both the amplitude and the duration of each pulse, the apparatus 10 may be used to determine the quality of glass having either a high optical distortion, or a mask placed beyond the focal length of the distortion.

Figure 5:
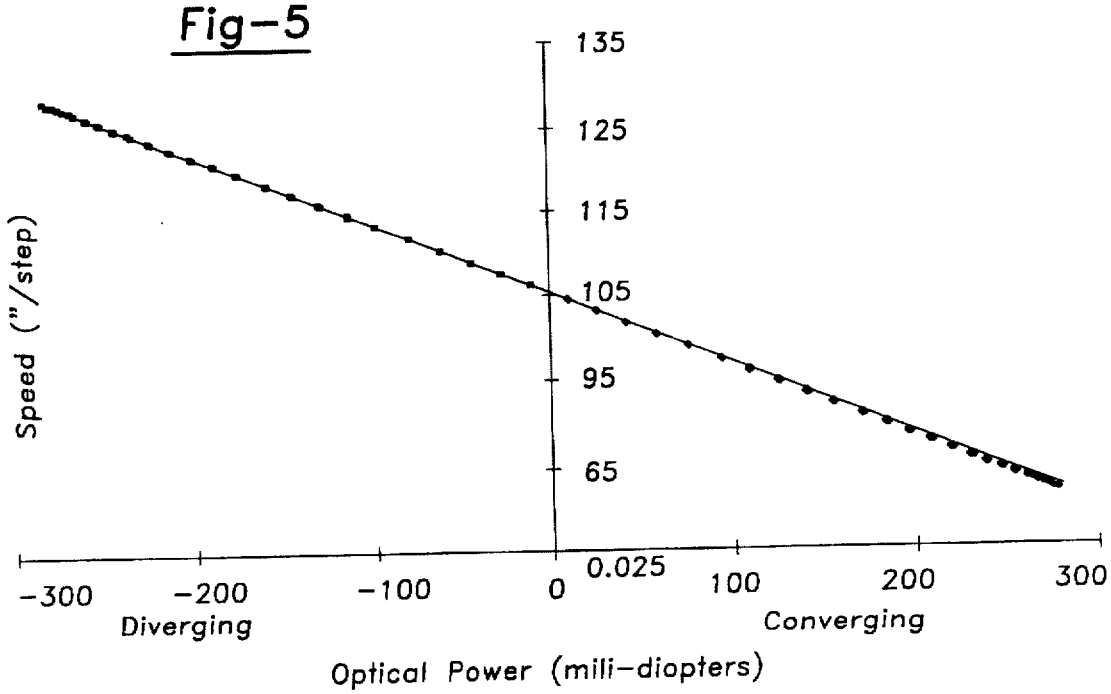
FIG. 5 is a graph of beam speed versus optical power.

The invention relies on a speed measurement of the light beam as it travels from one area of the mask to the other area. The rate of travel is inversely proportional to the distortion within the glass. Shown in FIG. 5 is an analytical representation of the beam's speed versus the optical power of the glass. The speed of the beam is measured in inches/second and the distortion in mili-diopters. Areas of the glass that form diverging distortion are represented as negative optical power and areas of the glass that form converging distortion are represented as areas having positive optical power.

The invention has been described primarily as a method of measuring the optical distortion within a glass sheet. It is also useful for measuring the surface irregularities along a sheet using the same method and apparatus as described. These and other variations modifications and adaptations of the present invention are within the scope of the following claims.

I claim:

1. A method of determining the quality of flat glass sheet comprising the steps of:
    illuminating a rotating mirror with a light ray to form a moving ray and directing said light ray from said rotating mirror at an acute angle onto said glass sheet;
    positioning a mask having alternating opaque and transparent portions to receive light from said ray after striking said glass sheet;
    moving said ray from a first position of said sheet to a second position of said sheet and causing said light ray to move along said mask;
    collecting light passing through said mask;
    measuring the duration of said collected light; and
    correlating said measured duration to the quality of said glass sheet.

2. The method of claim 1, wherein said light ray passes through said glass sheet and said method determines the optical quality of said glass sheet.

3. The method of claim 1, wherein said light ray is reflected off of the surface of said glass sheet and said method determines the surface irregularities of said glass sheet.

4. The method of claim 1, wherein said acute angle is between 45 and 85 degrees.

5. The method of claim 1, wherein said light ray maintains a nearly constant angle to said glass sheet from said first position to said second position.

6. The method of claim 1, further comprising reflecting said light ray from said rotating mirror onto said glass sheet.

7. The method of claim 1, wherein said light is collected by an internally reflecting light pipe and transmitted to a light detector.

8. The method of claim 1, wherein said measured light forms pulses representing the presence and absence of light passing through said mask, said measuring step further comprising measuring both the duration of each pulse and the interval between pulses.

9. The method of claim 8, wherein said correlation step comprises comparing said measured duration and interval with known values to determine the quality of said glass sheet.

10. The method of claim 1, further comprising a semi-transparent portion between said transparent and opaque portions, light passing through said semi-transparent portion has a lower intensity than light passing through said transparent portion, and
    wherein said measuring step further comprises measuring the intensity of said collected light and said correlating step includes correlating said measured intensity to the quality of said glass sheet.

11. The method of claim 1, further comprising the step of; converting said duration measurement into a velocity measurement, said duration measurement being inversely proportionally to the velocity of the light as it travels along said mask.

12. The method of claim 11, further comprising the step of converting said velocity measurement to the refractive index of said glass sheet.

13. A method of determining the optical quality of flat glass sheet comprising the steps of:

illuminating a rotating a mirror with a laser light ray and reflecting said light ray to a first surface of said glass sheet;

illuminating a line along said glass sheet with a light ray at a constant angle between 45 and 85 degrees to said glass sheet;

positioning a mask having alternating opaque and transparent portions opposite a second surface of said glass sheet to receive light that passes through said glass sheet;

moving said ray from a first position of said sheet to a second position of said sheet and causing said light ray to move along said mask, said ray is interrupted by the opaque portions of said mask and forms light pulses;

collecting said light pulses passing through said mask with an internally reflecting light pipe and transmitting said collected light pulses to a light detector;

measuring the duration and interval of said collected light pulse with said detector;

comparing said measured interval and duration with known values to determine the quality of said glass sheet and identifying defects in said glass sheet by identifying variations between said measured duration and interval and said known values, and displaying the quality of said glass sheet on a display means.

14. The method of claim 13, further comprising a semi-transparent portion between said transparent and opaque portions, light passing through said semi-transparent portion has a lower intensity than light passing through said transparent portion and wherein said measuring step further comprises measuring the intensity of said collected light and said comparison step includes determining the velocity of said light as it moves along said mask, and said velocity is proportional to the optical power of said glass sheet.

15. An apparatus for determining the optical quality of flat glass sheet comprising:

a laser casting a light ray onto a rotating a mirror;

a reflector reflecting said light ray onto a first surface of said glass sheet and illuminating a line along said glass sheet at a constant angle between 45 and 85 degrees to said glass sheet;

a mask having alternating opaque and transparent portions placed opposite a second surface of said glass sheet receiving light that passes through said glass sheet, said light ray moving from a first position of said sheet to a second position of said sheet and causing light that passes through said glass sheet to move along said mask, said passing light being interrupted by the opaque portions of said mask to form light pulses;

an internally reflecting light collector passing said collected light pulses to a light detector, said light detector measuring the duration and interval of said collected light pulses;

comparison means comparing said measured duration and interval with know values to determine the quality of said glass sheet and identifying defects in said glass sheet by identifying variations between said measured duration and interval and said known values; and display means displaying the quality of said glass sheet.

* * * * *